(12) United States Patent
Foltz et al.

(10) Patent No.: US 7,296,571 B2
(45) Date of Patent: Nov. 20, 2007

(54) ELECTRICAL CAUTERY-OXYGEN SAFETY DEVICE

(76) Inventors: James W. Foltz, 8351 E. Corrine Dr., Scottsdale, AZ (US) 85260; Michael E. Lubin, 10401 N. 22nd Pl., Phoenix, AZ (US) 85028

( * ) Notice: Subject to any disclaimer, the term of this patent is extended or adjusted under 35 U.S.C. 154(b) by 779 days.

(21) Appl. No.: 10/856,205

(22) Filed: May 27, 2004

(65) Prior Publication Data
US 2005/0021021 A1 Jan. 27, 2005

Related U.S. Application Data

(60) Provisional application No. 60/474,131, filed on May 28, 2003.

(51) Int. Cl.
*A61M 11/00* (2006.01)
(52) U.S. Cl. .................. 128/202.24; 606/35
(58) Field of Classification Search .......... 128/202.22, 128/204.18–204.26, 848, 205.25; 606/34–52
See application file for complete search history.

(56) References Cited

U.S. PATENT DOCUMENTS

| | | | |
|---|---|---|---|
| 4,184,492 A | | 1/1980 | Meinke et al. |
| 4,563,570 A | | 1/1986 | Johns |
| 5,312,327 A | | 5/1994 | Bales et al. |
| 5,803,065 A | * | 9/1998 | Zdrojkowski et al. . 128/204.23 |
| 6,382,207 B1 | | 5/2002 | Giuffre et al. |
| 2006/0058784 A1 | * | 3/2006 | Gedebou ............. 606/45 |
| 2006/0069387 A1 | * | 3/2006 | Gedebou ............. 606/45 |

OTHER PUBLICATIONS

Mattucci, et al., "The Prevention of Fire During Oropharyngeal Electrosurgery", ENT-Ear, Nose & Throat Journal, Feb. 2003, pp. 107-109, vol. 82, No. 2, United States.
Chih-Cheng, et al, "Endotracheal Fire Induced by Electrocautery during Tracheostomy—A Case Report", Acta Anaesthesiol Sin, Dec. 2002, pp. 209-213, vol. 40, China.
Baur, et al., "Electrocautery-Ignited Endotracheal Tube Fire: Case Report", British Journal of Oral & Maxillofacial Surgery, Apr. 1999, pp. 142-143, vol. 38, No. 2, Scotland.
Moyer, Paula, "Operating Room Fires; How to Prevent and Minimize Spread", Today's Surgical Nurse, Nov./Dec. 1998, pp. 13-40, vol. 20, No. 6, United States.

(Continued)

*Primary Examiner*—Steven O. Douglas
(74) *Attorney, Agent, or Firm*—Gallagher & Kennedy, P.A.; Thomas D. MacBlain

(57) ABSTRACT

Operating room fires are prevented by a safety interlock that disables instrumentalities (such as an electrical cautery device) capable of igniting a fire in the presence of oxygen and a fuel source or combustible material such as skin, hair and/or prep agents containing alcohol. Removal of, e.g., the cautery device is sensed by a sensor to disable an oxygen source supplying oxygen to a patient and set a timer. Electrical activation of the cautery device only is permitted upon timing-out of the timer, which timing out is set for a time when oxygen will have cleared from the patient's immediate surroundings. A further safety feature is provided in a further timing, by the same or another timer, of the time during which the patient has been deprived of oxygen. After a short duration, then, the cautery (or other) device is denied electrical power and oxygen is permitted to flow again to the patient.

8 Claims, 4 Drawing Sheets

OTHER PUBLICATIONS

Thompson, et al., "Fire in the Operating Room During Tracheostomy", Southern Medical Journal, Mar. 1998, pp. 243-247, vol. 91, No. 3, United States.

Keller, Christopher et al., "Endotracheal Tube Safety During Electrodissection Tonsillectomy", Arch Otolaryngol Head Neck Surg, Jun. 1992, pp. 642-645 + 1367, United States.

Lew et al, "Endotracheal Tube Ignition by Electrocautery During Tracheostomy . . . ", Journal of Forensic Science, Sep. 1991, pp. 1586-1591, vol. 36, No. 5, United States.

Wesley, et al., "Use of Venturi Entrainment Mask for High-Flow Ventilation of Patients . . . ", Ophthalmic Surgery, Feb. 1981, vol. 12, No. 2, pp. 85-88, United States.

Magruder, et al., "Fire Prevention During Surgery", American Medical Association Publication, Aug. 1970, vol. 84, pp. 237, United States.

Wolf, Gerald, "Decreasing Airway Fire Risk During Laser Surgery Is Aim of New Subcommittee", ASTM Stadardization News, Dec. 1990, pp. 20-22, United States.

* cited by examiner

ELECTRICAL CAUTERY-OXYGEN SAFETY DEVICE

CROSS REFERENCE TO RELATED APPLICATIONS

This application claims priority from the provisional patent application Ser. No. 60/474,131 filed May 28, 2003 in the name of James W. Foltz and Michael E. Lubin entitled "Electrical Cautery-Oxygen Safety Device" incorporated herein by reference.

BACKGROUND OF THE INVENTION

This device is intended to aid in reducing the risk of operating room fires. An increasing number of incidents have been reported involving operating room fires occurring during surgery, particularly associated with surgery involving the head and neck area. The cause of the fires and the nature of the fire hazards have been investigated and to a large extend determined. Fire results when three elements are combined, an oxidizer, a combustible material, and an ignition source. In the surgical setting, an oxygen rich environment is created near the patient's head or in the patient's mouth, throat and/or nose due to oxygen (or nitrous oxide) flow to the patient through nasal prongs, a mask, or to a lesser extent, an endotracheal tube. The combustible material is the patient's hair and skin, especially when prepped with flammable prep agents such as those containing alcohol. The ignition source is a heat producing surgical tool such as an electrosurgical pencil, electrical cautery device or a laser. The risk is frequently further increased by the practice of draping in such a way that the oxygen rich environment is contained in a smaller volume surrounding the patient's head.

Protocols intending to decrease the risk of operating room fires have been aimed at changing surgical and anesthesia habits. Different preps have been developed, and surgical personnel have been cautioned regarding occlusive draping. It has been proposed that the need for electrical cautery by the surgeon should, if possible, be anticipated so that the anesthesiologist might momentarily stop the flow of oxygen-rich gas to the patient. Thus the oxygen level surrounding the operating field would be lowered by the time the electrical cautery spark about to be used occurred. Protocols which depend on the surgeon anticipating the need for cautery, notifying the anesthesiologist, and ultimately waiting for verbal clearance before applying the cautery are likely to be futile. They are likely to be forgotten or ignored by the busy surgeon. Similar fire risks can be encountered in laser surgery.

There is thus a need to automatically stop the flow of oxygen when the electrical cautery or other heat source such as a laser is about to be used and then not allow the heat source's operation until adequate time has passed to insure that the oxygen level in the field is at a safe level, and the risk of fire has been greatly lowered.

SUMMARY OF THE INVENTION

In accordance with this invention a system is provided that cuts off the supply of oxygen-rich gas to a patient before a heat generating surgical tool is employed. As used herein "oxygen-rich" means pure oxygen, oxygen enriched air, nitrous oxide or another gas delivered to a patient and capable of creating a region heightened oxygen content on or around the patient. To prevent or substantially reduce the occurrence of operating room fires, a time lapse is provided between the turn off of oxygen-rich gas to a patient and the time at which heat generating surgical tool can be activated. By "operating room" is meant any hospital operating room or a doctor or other medical practitioner's office outfitted for surgery. Also, although described in particular as applicable to hospitals and medical practices treating human patients, the benefits of the invention apply to veterinarian practices as well; "patient" then may be a pet or other animal, as well as a human patient.

In accordance with this invention, a device is provided that is separate from and augments the heat producing surgical tool. A preferred exemplary embodiment is described in connection with an electrical cautery device. An electrical cautery device employs a high frequency current generator which is generally unipolar. It requires a grounding plate attached to the patient and a hand held implement or handpiece with an electrode and a switch. In one preferred embodiment of the invention the new safety device comprises a control circuit electrically connected between the cautery tool or other heat generating surgical tool and its electrical supply. The control circuit receives the output of the surgical tool electrical supply. The surgical tool electrically connects to the new device of this invention, allowing current to it to be interrupted by the control circuit.

In the exemplary preferred embodiment described, a holder for the surgical tool, which is ordinarily a simple plastic holster designed to be secured to the OR technician's instrument stand, is reconfigured to contain a proximity sensor. This may be, for example, a known electromagnetic metal sensor. The cautery handpiece's metallic blade is sensed by the proximity sensor to detect the presence of the handpiece. Other sensors are as readily usable. These include, without limitation, known optical detectors, mechanical switches, capacitive switches, etc.

In accordance with this invention the control circuit has an output that controls a gas valve placed at the anesthesia machine output flow delivering the oxygen rich gas to the patient.

The safety device of this invention functions as follows: When the surgeon removes the surgical tool from the holder in preparation for its use on the patient that is sensed by the sensor and the control circuit responds to the removal from near the proximity sensor and turns off the flow of oxygen to the patient. The heat producing surgical tool is disabled for a set time, possibly 10 to 15 seconds to allow the oxygen level to drop. The tool is then enabled and can be used. For protection of the patient's oxygenation, in one preferred embodiment if the tool is used for more than, say, 45 seconds, the current flow to the tool is interrupted and the oxygen circuit is reopened. The handpiece then needs to be returned to its holder to reestablish the cycle. Preferably an additional delay is provided after return of the handpiece, say one minute, to prevent repeat cycling and resultant decrease in oxygenation to the patient.

Preferably also the oxygen valve includes a mechanical override valve which is utilized to restore oxygen flow in the event of a system failure, as well as an indicator such as an LED showing the status of oxygen flow.

DETAILED DESCRIPTION

Figure 1:
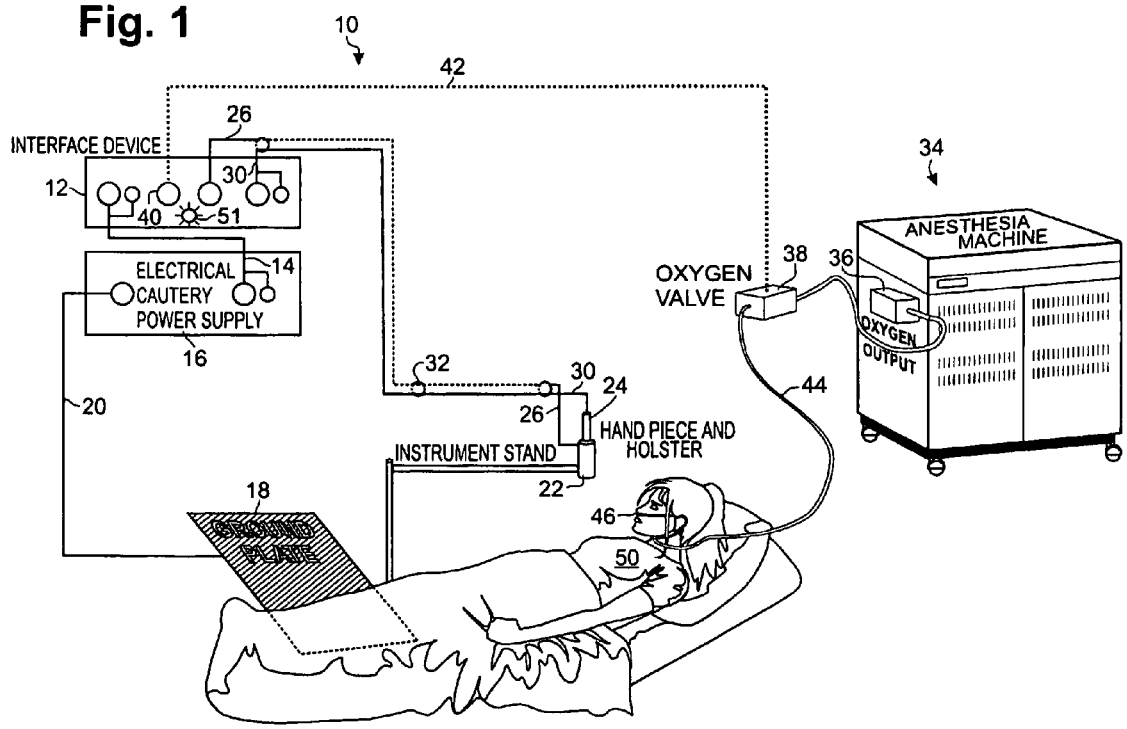
FIG. 1 is a schematic partially in block diagram form of the safety system of this invention installed.
Figure 2:
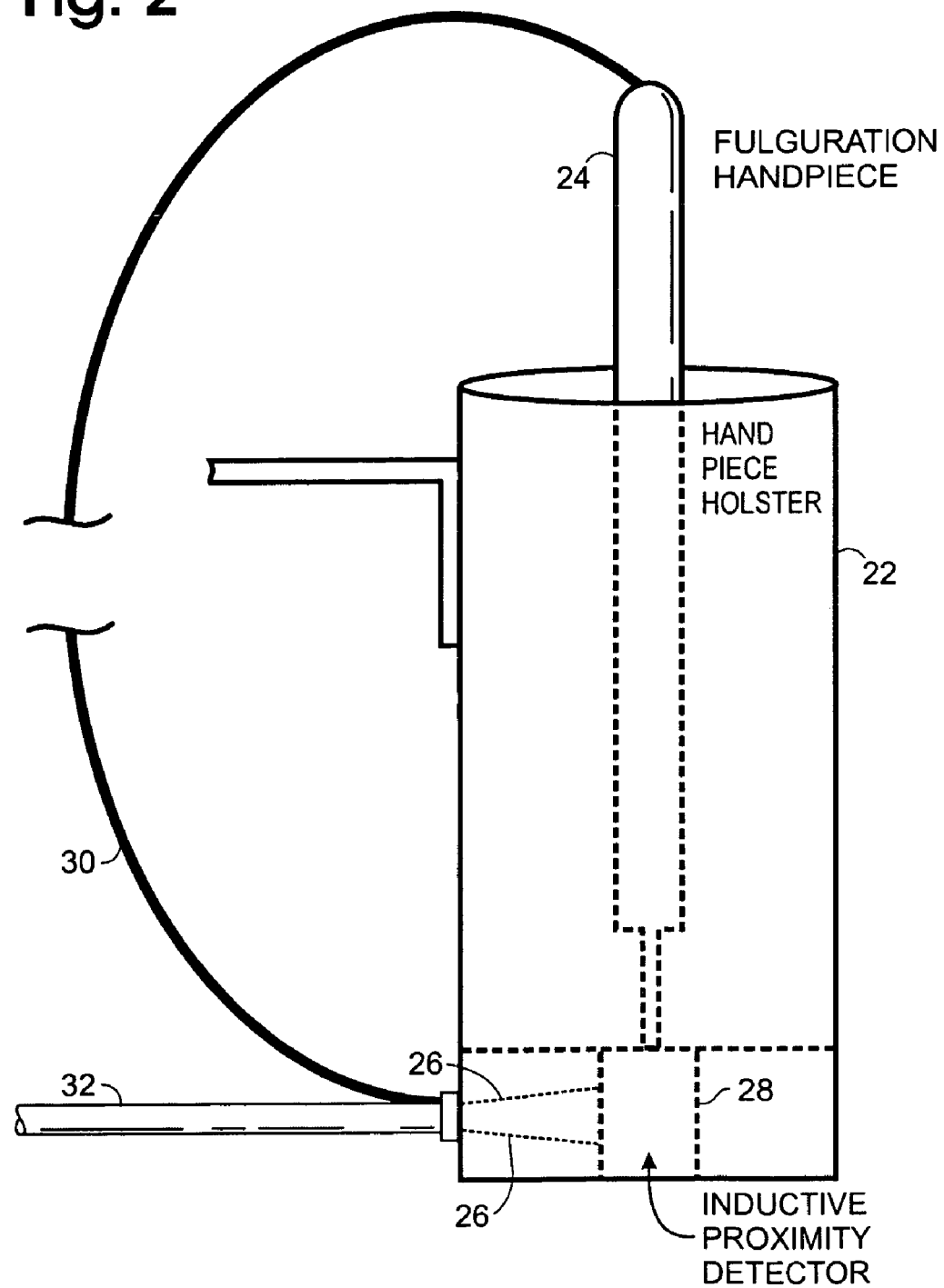
FIG. 2 is a diagrammatic illustration of a reconfigured surgical instrument holster having a sensor for use with the system of this invention.

As shown in FIG. 1, an installation 10 implementing the invention includes a control circuit 12 connected to an output 14 of a power supply 16 for a surgical instrument or tool 24, in the exemplary embodiment an electrical cautery. A ground plate 18 is shown connected at 20 to the supply 16 for application to the patient. A holster 22 for the tool 24 has an electrical connection 26 from proximity sensor secured thereon (28 in FIG. 2) to the control circuit 12. The proximity sensor, shown, or indeed another kind of detector, is used to detect when the cautery 74 is removed from its holster. An electrical connection 30 from the control circuit to the instrument or tool 24 is shown running along a combined handpiece cable 32 with the wire or wires of the proximity device electrical connection 26.

An anesthesia machine 34 in FIG. 1 has an oxygen output 36 connected to an electrically operated oxygen valve 38. The oxygen output supplies oxygen (or more accurately oxygen-enriched air) to the patient, ordinarily under the control of an attendant anesthesiologist. A control output 40 of the control circuit 12 is connected at 42 to the oxygen valve 38 to open and close that valve, alternately supplying and cutting off the supply of oxygen-rich gas through a tube 44 to, e.g. nasal prongs 46 supplying oxygen to a patient 50. An LED 51 on the control circuit 12 indicates that the valve 38 is open and that oxygen is flowing.

Figure 3:
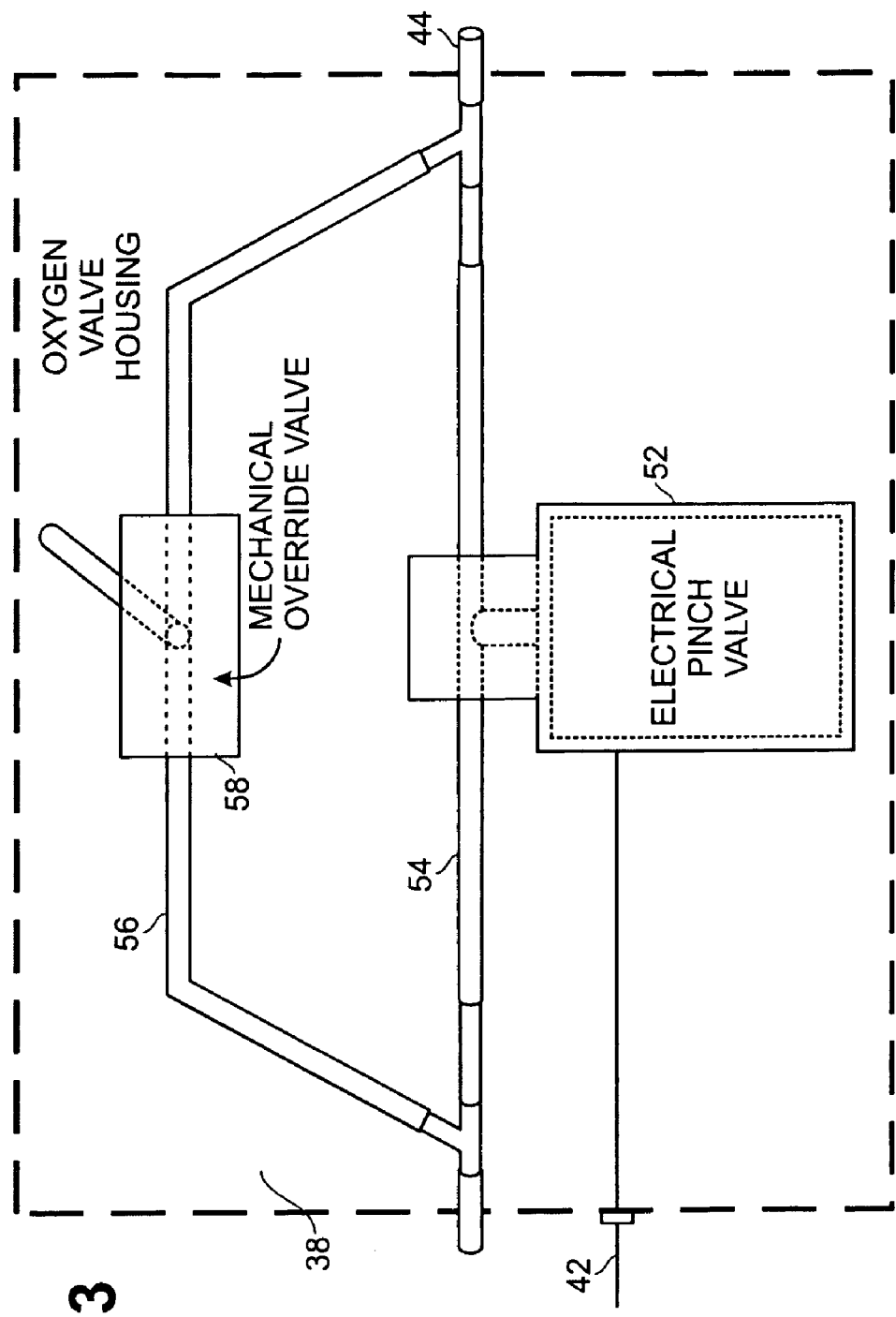
FIG. 3 is an oxygen valve for use in the system of the invention.

The oxygen valve 38 is shown in greater detail in FIG. 3. The valve 38 may contain a solenoid operated normally open pinch valve 52 alternately pinching closed and opening a flexible tube 54 in the path of oxygen flow from the anesthesia machine to the patient. Connected in parallel with the tube 54 is shown an oxygen path 56 under the control of a manually operated override valve 58. This too can be a pinch valve, this one normally closed The control circuit 12 of FIG. 1 can be readily implemented in any of a number of easily accomplished embodiments such as that shown in the functional block diagram of FIG. 4. There a programmed digital controller 60 controls a pair of semiconductor switches 62 and 64 that supply electrical power from the power supply 66 to the oxygen valve 38 of FIG. 3 and the surgical tool 24 of FIGS. 1 and 2. An analog to digital converter (ADC) 68, for example, which may be incorporated in the proximity sensor 29, can provide an input to the microcontroller 60 upon receiving a signal from the proximity sensor indicating the removal of the tool 24 from its holster 22. The proximity sensor can be a known, commercially available sensor capable of sensing the proximity or lack of proximity of a metal blade of the surgical tool by its effect on a generated magnetic field. The microcontroller typically would supply signals to the switches 62 and 64 at times programmed into the microcontroller such that after receipt of a signal from the analog to digital converter 68 the switch 64 is turned on to supply the surgical tool only after the passage of, for example 10 or 15 seconds. The switch 62 is turned on immediately upon receipt of the ADC output by the controller 60 to stop the flow of oxygen. The output to the switch 62, however, times out as described above to release the pinch valve and permit oxygen to flow. At that time the switch 64 is opened simultaneously with the turn on of switch 62 to turn off the surgical tool as oxygen again begins to flow. Finally, the microcontroller 60 is preferably programmed to delay any further turn on of the switch 64 for a period of time subsequent to the timing out of the maximum period for the cessation of oxygen flow. This period of time can be started to run by return of the tool 24 to the holster 22 as sensed by the sensor 28.

Figure 4:
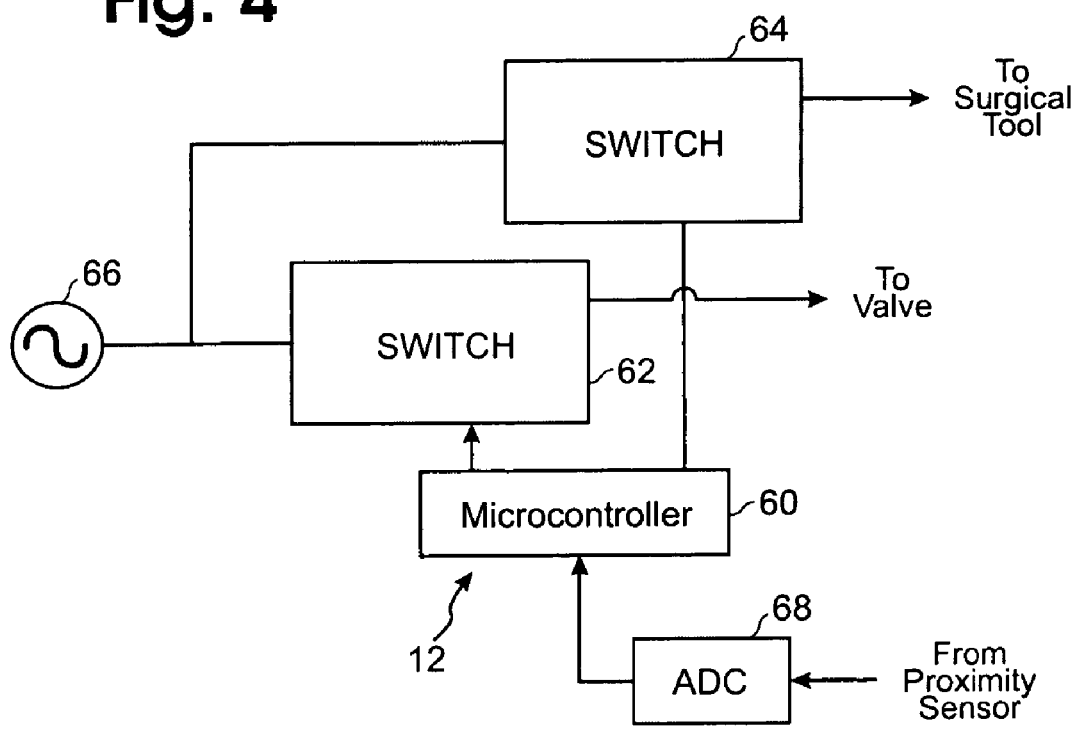
FIG. 4 is a control circuit block diagram of an exemplary control circuit for use in the system of FIG. 1.

Alternative arrangements to the exemplary control circuit 12 shown schematically in FIG. 4 can be fashioned using discrete logic elements and timing circuits arranged to accomplish the described control and timing functions, analog circuitry employing RC timing circuits, or even mechanical devices such as dashpots used in the timing of the valve and surgical tool switching. The sensor may be electromagnetic, optical or a simple mechanical or capacitive switch, without limitation. Alternatively, an on-off switch on the tool 24, mechanical or capacitive, can be the basis for activating interruption of oxygen and starting the timing during which the tool 24 was inoperable.

While one or more specific preferred embodiments have been described in this application, those skilled in the art will readily recognize modifications, variations and equivalents that do not depart from the spirit and scope of the subject invention, as set forth in the appended claims.

We claim:

1. A fire prevention apparatus for use in a medical setting where oxygen-rich gas is often supplied to a patient during a medical procedure; the apparatus comprising:
   (a) means for supplying oxygen-rich gas to a patient;
   (b) an electrically operable cut-off valve operative to interrupt the supply of oxygen-rich gas to the patient;
   (c) a receptacle for an electrically heated surgical tool;
   (d) a sensor associated with the receptacle for sensing the presence of the tool in the receptacle;
   (e) a control circuit comprising:
       (i) means responsive to the sensor signaling removal of the tool from the receptacle for operating the cut-off valve to interrupt the supply of oxygen; and
       (ii) means responsive to the sensor signaling removal of the tool from the receptacle to delay electrical activation of the tool for a period of time during which oxygen has been interrupted.

2. The fire prevention apparatus of claim 1, wherein the control circuit further comprises:
   (iii) means for automatically interrupting electrical power to the tool after a predetermined time during which the oxygen supply has been interrupted.

3. The fire prevention apparatus of claim 1, further comprising a manual override valve connected to deliver oxygen-rich gas past the cut-off valve to a patient upon manual activation.

4. The fire prevention apparatus of claim 2, further comprising timing means responsive to the cutoff of oxygen to a patient to activate the cut-off valve in an oxygen-rich gas supplying condition after a predetermined period.

5. The fire prevention apparatus of claim 4, wherein the timing means responsive to the cutoff of oxygen is further operative to interrupt electrical power delivered to the tool.

6. The fire prevention apparatus of claim 5, further comprising timing means operative to set a delay of re-energizing the tool subsequent to an interruption of electrical power to the tool by the timing means responsive to the cutoff of oxygen, thereby to assure satisfactory oxygenation of a patient.

7. The fire prevention apparatus of claim 6, wherein the timing means operative to set a delay of re-energizing the tool is operatively connected with the sensor to begin a timing period of delay of re-energizing the tool upon return of the tool to the receptacle.

8. A surgery fire prevention system including:
(a) a heat producing electrically activated surgical tool,
(b) a control circuit,
(c) an electrically operable valve connected in flow controlling relation to a path of oxygen-rich gas supply for a surgical patient,
(d) a tool receptacle for receiving the electrically activated surgical tool when the tool is not in use,
(e) a detector for detecting removal of the tool from the receptacle,
(f) the detector having an output connected as an input to the control circuit,
(g) the control circuit having an output for supplying electrical power to the tool in response to a detector output indicating removal of the tool from the receptacle,
(h) the control circuit having a further output for operating the electrically operable valve, and
(i) the control circuit being operative to close the electrically operative valve and stop the flow of oxygen-rich gas in response to the output from the detector indicating removal of the tool from the receptacle and to delay the output for supplying electrical power to the tool for a predetermined time period following removal of the tool from the receptacle and closure of the valve.

* * * * *